United States Patent
Gazeau et al.

(10) Patent No.: US 12,098,355 B2
(45) Date of Patent: Sep. 24, 2024

(54) FLUID SYSTEM FOR PRODUCING EXTRACELLULAR VESICLES AND RELATED METHOD

(71) Applicants: UNIVERSITE DE PARIS, Paris (FR); CENTRE NATIONAL DE LA RECHERCHE SCIENTIFIQUE (CNRS), Paris (FR); GENETHON, Evry (FR)

(72) Inventors: Florence Gazeau, Kremlin Bicetre (FR); Amanda Karine Andriola Silva, Igny (FR); Otto-Wilhelm Merten, Crespieres (FR); Claire Wilhelm, Velizy-Villacoublay (FR); Max Piffoux, Paris (FR)

(73) Assignees: UNIVERSITE DE PARIS, Paris (FR); CENTRE NATIONAL DE LA RECHERCHE SCIENTIFIQUE (CNRS), Paris (FR); GENETHON, Evry (FR)

(*) Notice: Subject to any disclaimer, the term of this patent is extended or adjusted under 35 U.S.C. 154(b) by 0 days.

(21) Appl. No.: 16/627,013

(22) PCT Filed: Jun. 29, 2018

(86) PCT No.: PCT/EP2018/067704
§ 371 (c)(1),
(2) Date: Dec. 27, 2019

(87) PCT Pub. No.: WO2019/002608
PCT Pub. Date: Jan. 3, 2019

(65) Prior Publication Data
US 2020/0385665 A1    Dec. 10, 2020

(30) Foreign Application Priority Data
Jun. 30, 2017  (FR) ...................... 1756183

(51) Int. Cl.
C12M 3/06 (2006.01)
C12M 1/00 (2006.01)
C12M 1/12 (2006.01)

(52) U.S. Cl.
CPC ............ *C12M 27/14* (2013.01); *C12M 25/16* (2013.01); *C12M 29/04* (2013.01)

(58) Field of Classification Search
CPC ....... C12M 27/14; C12M 25/16; C12M 29/04
(Continued)

(56) References Cited

U.S. PATENT DOCUMENTS

| 4,806,484 A | 2/1989 | Petrossian et al. |
| 2016/0355776 A1 | 12/2016 | Lipkens et al. |
| 2017/0137774 A1 | 5/2017 | Lipkens et al. |

FOREIGN PATENT DOCUMENTS

| GB | 2163453 A * | 2/1986 | ............ C12M 25/16 |
| WO | WO-03002590 A2 * | 1/2003 | ............ B01F 11/008 |

(Continued)

OTHER PUBLICATIONS

Ozturk et al., An Approach for Assessing Turbulent Flow Damage to Blood in Medical Devices, Journal of Biomechanical Engineering, (2017), Jan. 2017, vol. 139 (Year: 2017).*

(Continued)

*Primary Examiner* — Michael L Hobbs
*Assistant Examiner* — Lenora A Abel
(74) *Attorney, Agent, or Firm* — Maier & Maier, PLLC

(57) ABSTRACT

A fluidic system for producing extracellular vesicles from producer cells, including at least one container, a liquid medium contained by the container and producer cells, characterised in that it also includes microcarriers suspended in the liquid medium, the majority of producer cells being adherent to the surface of the microcarriers, and a liquid medium agitator, the agitator and the dimensions of the
(Continued)

container being adapted to control a turbulent flow of the liquid medium in the container.

2 Claims, 8 Drawing Sheets

(58) Field of Classification Search
USPC .................................................. 435/286.7
See application file for complete search history.

(56) References Cited

FOREIGN PATENT DOCUMENTS

| WO | 2015048566 A1 | 4/2015 | |
|---|---|---|---|
| WO | WO-2016168680 A1 * | 10/2016 | ......... A61K 39/0011 |
| WO | 2017076924 A1 | 5/2017 | |

OTHER PUBLICATIONS

Xu et al., Motion of inertial particles with size larger than Kolmogorov scale in turbulent flows, Physica D, 237, (2008), 2095-2100 (Year: 2008).*

Andaloussi et al., Extracellular vesicles: biology and emerging therapeutic opportunities, p. 347, vol. 12 (Year: 2013).*

International Search Report issued on Sep. 25, 2018 in corresponding International application No. PCT/EP2018/067704; with English language translation, 4 pages.

Max Piffoux Et al.; 2017, "Extracellular Vesicle Production Loaded with Nanoparticles and Drugs in a Trade-off between Loading, Yield and Purity: Towards a Personalized Drug Delivery System", Advanced Biosystems; 12 pgs.

Dionysios C. Watson, et al., "Efficient production and enhanced tumor delivery of engineered extracellular vesicles", Biomaterials, Oct. 2016; 27 pgs.

A. N. Kolmogorov; "The Local Structure of Turbulence in Incompressible Viscous Fluid for Very Large Reynolds Numbers", Proceedings of the Royal Society; Mathematical, Physical & Engineering Sciences; London; 1991; 6 pgs.

Genwen Zhou, et al.; "Impact of Tank Geometry on the Maximum Turbulence Energy Dissipation Rate for Impellers", AICHE Journal; Sep. 1996; vol. 42, No. 9; 15 pgs.

Alvin W. Nienow et al., "Impeller Power Nos. in Closed Vessels", Industrial & Engineering Chemistry Process Design and Development; 1971; vol. 10; No. 1; 3 pgs.

Japanese Office Action dated Mar. 15, 2022, in corresponding Japanese Application No. 2020-522409, 13 pages (with English translation).

Enomura et al., "Development and Applicability of a New Medialess Disperser", Coloring Materials, vol. 75, No. 12, 2022, pp. 586-591 (with English Abstract).

Notice of Preliminary Rejection dated Sep. 7, 2022, in corresponding Korean Patent Application No. 10-2020-7002967, 18 pages (with English Translation).

Rani et al., "Mesenchymal Stem Cell-derived Extracellular Vesicles: Toward Cell-free Therapeutic Applications", The American Society of Gene & Cell Therapy, Molecular Therapy, May 2015, vol. 23, No. 5, pp. 812-823.

Lee et al., "Scale-up and manufacturing of cell-based therapies", ECI symposium, [online], Jun. 26, 2017, [Searched on Sep. 7, 2022], Web:<URL: http://www.dc.engconfintl.org/cellbasedtherapies_v/62/, 2 pages.

Fábio G. Teixeira et al., "Modulation of the Mesenchymal Stem Cell Secretome Using Computer-Controlled Bioreactors: Impact on Neuronal Cell Proliferation, Survival and Differentiation", Scientific Reports, vol. 6, No. 27791; Jun. 15, 2016; pp. 1-14.

* cited by examiner

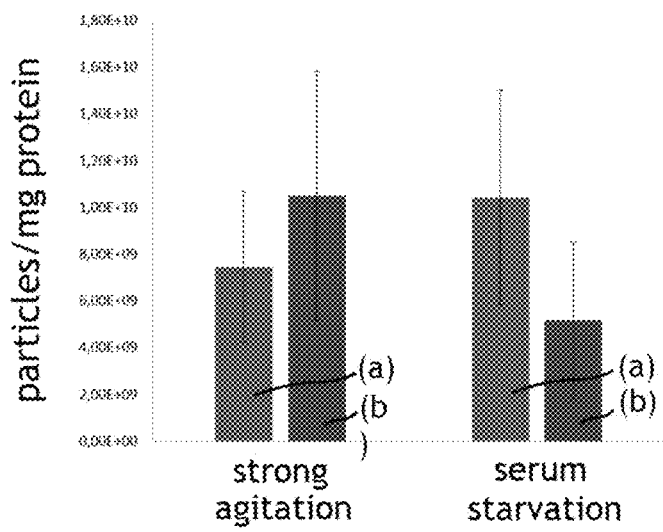
Figure 17
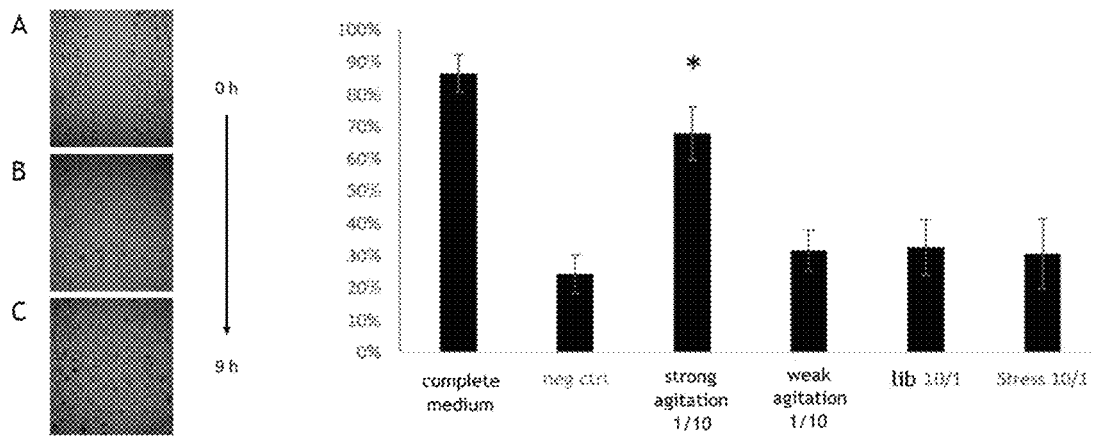
Figure 18
Figure 19
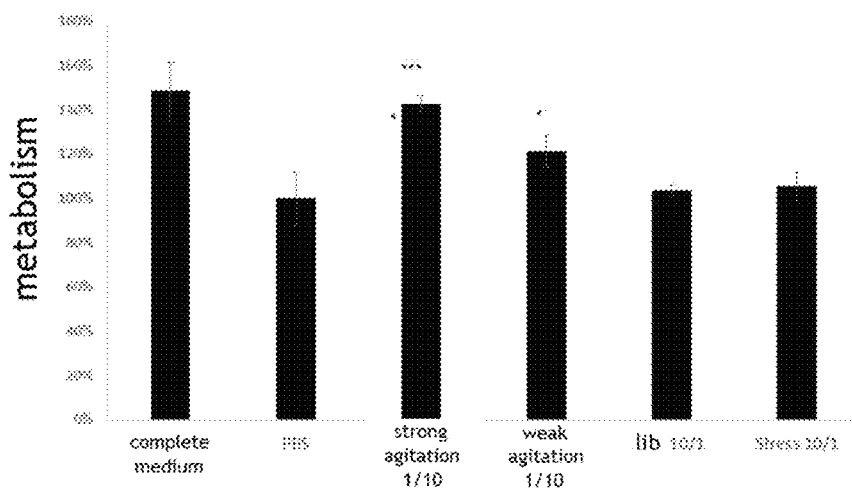
Figure 20

FLUID SYSTEM FOR PRODUCING EXTRACELLULAR VESICLES AND RELATED METHOD

FIELD

The invention relates to a system for producing extracellular vesicles from producer cells, a method for producing and recovering such vesicles and vesicles produced by such a system, for example used in cell therapy and in regenerative medicine.

BACKGROUND

Cells are known to release extracellular vesicles into their environment, for example, in vivo, into the biological fluids of an organism. Extracellular vesicles have been identified as efficient means for delivering drugs, in a personalised or targeted manner, to the human body. First, they have a native biocompatibility and an immune tolerance. They can also comprise theranostic nanoparticles, allowing both to image certain parts of the body and to deliver active ingredients having therapeutic functions. Extracellular vesicles also have an intercellular communication function: they allow, for example, transporting lipids, membrane and cytoplasmic proteins and/or nucleotides of the cell cytoplasm, such as mRNAs, microRNAs or long non-coding RNAs, between different cells.

Particularly, the use of extracellular vesicles may allow solving known problems during the therapeutic use of cells, such as cell replication, differentiation, vascular occlusions, the risks of rejection and the difficulties of storage and freezing. Consequently, there is an industrial need for the production of cell vesicles in sufficient amounts for a therapeutic use, in particular as a replacement or in addition to cellular therapies.

To this end, Piffoux et al. (Piffoux, M., Silva, A. K., Lugagne, J. B., Hersen, P., Wilhelm, C., & Gazeau, F., 2017, *Extracellular Vesicle Production Loaded with Nanoparticles and Drugs in a Trade-off between Loading, Yield and Purity: Towards a Personalized Drug Delivery System*, Advanced Biosystems) describe the comparison of different methods for producing extracellular vesicles.

A first method consists in producing extracellular vesicles from endothelial cells of the umbilical cord vein (HUVEC), by subjecting these cells to hydrodynamic stresses mimicking the stresses exerted under physiological conditions within blood capillaries or under pathological conditions during stenosis of blood vessels. These stresses are caused by the passage of producer cells into microfluidic channels, for four hours. A microfluidic chip comprises two hundred channels wherein cells are transported in a laminar flow, to produce vesicles in a parallelised manner.

However, this method has dimensioning problems: the amounts of vesicles produced by a microfluidic chip are not adapted to the amounts required for the abovementioned applications. In addition, the yield of extracellular vesicles produced per cell introduced into such a chip (about $2 \times 10^4$ vesicles per cell) is much lower than the maximum theoretical yield of vesicles produced by a cell, for example of the order of $3.5 \times 10^6$ vesicles per cell for an MSC-type cell (acronym for mesenchymal stem cell). Finally, this method requires compliance with the standards called G.M.P. (acronym for Good Manufacturing Practises), necessary for the manufacture of drugs.

A second method commonly used in the literature and described by Piffoux et al. consists in cultivating HUVECs in a culture medium of the DMEM type (acronym for Dulbecco's Modified Eagle's Medium) without serum, for three days (called starvation, or serum starvation technique). The absence of serum leads to a cellular stress triggering the release of vesicles by the producer cells. This method has a higher yield and allows producing a greater amount of vesicles than the method using a microfluidic chip (about $4 \times 10^4$ vesicles per producer cell). However, the calculated yield corresponds to a production time much longer than the production time of the previous method. This method does not allow producing an amount of extracellular vesicles sufficient for the abovementioned applications. Finally, this method does not allow producing vesicles continuously since it induces the death of the cells.

Watson et al. (Watson, D. C., Bayik, D., Srivatsan, A., Bergamaschi, C., Valentin, A., Niu, G., . . . & Jones, J. C., 2016, *Efficient production and enhanced tumour delivery of engineered extracellular vesicles*, Biomaterials, 105, 195-205) describe a vesicle production method allowing to increase the amount of vesicles produced. This method consists in cultivating HEK293-type cells in culture flasks, then in hollow fibre membranes. The central passage of the hollow fibres allows the culture medium to be conveyed to the producer cells. The producer cells are first seeded around this passage, where they produce vesicles in an inter-fibre space. The liquid medium comprised in the inter-fibre space is collected three times a week, allowing to produce about $3 \times 10^{12}$ vesicles in several weeks, for very large amounts of seeded cells, for example of the order of $5 \times 10^8$ cells, resulting in a yield of about 6000 extracellular vesicles per cell and a very low purity ratio (for example $1.09 \times 10^9$ particles per microgram of proteins). However, this production is not high enough and too slow regarding the aforementioned applications. In addition, this method is described using producer cells corresponding to a cell line which is particularly resistant to the culture in a serum-free medium: this method may not be transposable to a production of vesicles by producer cells such as stem cells, for example human stem cells, less resistant and particularly suitable for the targeted therapeutic applications.

SUMMARY

A purpose of the invention is to propose a solution for producing large amounts of extracellular vesicles from producer cells, faster than with the known methods, under conditions which comply with the G.M.P standards. Another purpose of the invention is to propose a solution allowing to increase the yield of the vesicle production system, that is to say the ratio between the number of produced vesicles and the number of producer cells introduced into the production system. Another purpose of the invention is to propose a system adapted to produce extracellular vesicles from a wide range of adherent producer cells, regardless of the resistance of the type of cell introduced into the production system and resistant or not to a serum starvation. Another purpose of the invention is to propose a solution for continuously producing and recovering extracellular vesicles. Finally, another purpose of the invention is to simplify the structure of the fluidic system for the production of vesicles and to reduce the manufacturing cost thereof.

Particularly, an object of the invention is a fluidic system for producing extracellular vesicles from producer cells, comprising at least one container, a liquid medium contained by the container and producer cells, characterised in that it also comprises microcarriers suspended in the liquid medium, the majority of producer cells being adherent to the surface of the microcarriers, and a liquid medium agitator, the agitator and the shape and dimensions of the container being adapted to the generation of a turbulent flow of the liquid medium in the container.

It is understood that with such a system, it is possible to produce vesicles in large amounts, and in a system adapted to the G.M.P standards. It is also understood that such a system is simpler and less expensive to manufacture than the systems known for producing extracellular vesicles.

The invention is advantageously supplemented by the following features, taken individually or in any one of their technically possible combinations:

- the agitator of the liquid medium and the dimensions of the container are adapted to control a flow of the liquid medium, the Kolmogorov length of the flow being less than or equal to 75 µm, and preferably 50 µm;
- the fluidic system comprises an output and a connector connected to the output, the connector being capable of comprising liquid medium and extracellular vesicles;
- the agitator is a rotary agitator whose rotation speed(s), shape, size are adapted, with the shape and the dimensions of the container, to the generation of a turbulent flow of the liquid medium in the container;
- the microcarriers are microbeads, the diameter of the microbeads being comprised between 100 µm and 300 µm;
- the fluidic system comprises a separator of extracellular vesicles, which is fluidly connected to the container so as to be capable of reintroducing a vesicle-depleted liquid medium into the container.

Another object of the invention is a method for ex vivo production of extracellular vesicles from producer cells, comprising:

- controlling an agitator causing a turbulent flow of a liquid medium in a container, the container comprising an output, the liquid medium comprising producer cells adhering on the surface of the microcarriers, the microcarriers being suspended in the liquid medium, and
- collecting the liquid medium comprising extracellular vesicles at the output of the container.

The method is advantageously supplemented by the following features, taken individually or in any one of their technically possible combinations:

- the liquid medium is agitated for more than thirty minutes;
- the agitator is controlled to cause the liquid medium to flow, the Kolmogorov length of the flow being less than or equal to 75 µm and preferably 50 µm;
- a separator depletes part of the liquid medium collected at the output of the container of extracellular vesicles, and the part of the liquid medium is reintroduced into the container.

An object of the invention is also extracellular vesicles capable of being obtained by the extracellular vesicle production method object of the invention.

An object of the invention is also a pharmaceutical composition comprising extracellular vesicles capable of being obtained by the extracellular vesicle production method object of the invention.

Advantageously, the pharmaceutical composition comprising extracellular vesicles can be used in regenerative medicine.

Definitions

The term "extracellular vesicle" generally designates a vesicle released endogenously by a producer cell, whose diameter is comprised between 30 nm and 5000 nm. An extracellular vesicle particularly corresponds to an exosome and/or a microvesicle and/or a cellular apoptotic body.

The terms "microcarrier" and "microsupport" designate a spherical matrix allowing the growth of producer cells adhering to its surface or to the inside and whose maximum size is comprised between 50 µm and 500 µm, and preferably between 100 µm and 300 µm. The microcarriers are generally beads whose density is selected to be substantially close to that of the liquid culture medium of the producer cells. Thus, a gentle mixing allows the beads to remain suspended in the liquid culture medium.

BRIEF DESCRIPTION OF THE DRAWINGS

Other features and advantages will also emerge from the description which follows, which is purely illustrative and non-limiting, and should be read with reference to the appended figures, among which:

FIG. 17 illustrates the purity in extracellular vesicles given by the ratio between the number of particles and the mass of proteins, produced by the fluidic system in the liquid medium in comparison with the serum deprivation method for 72 h;

FIG. 18 illustrates the pro-angiogenic properties of a liquid medium comprising extracellular vesicles produced by the fluidic system;

FIG. 19 illustrates the pro-angiogenic properties of a liquid medium comprising extracellular vesicles produced by the fluidic system, the serum deprivation method or the spontaneous vesicle release method;

FIG. 20 illustrates the metabolic activity of cardiomyocytes (line H9C2) after one day of incubation in culture media comprising extracellular vesicles produced by the fluidic system;

DETAILED DESCRIPTION

Theoretical Elements

The Kolmogorov length (or Kolmogorov dimension or eddy length) is the length from which the viscosity of a fluid allows dissipating the kinetic energy of a flow of this fluid. In practise, the Kolmogorov length corresponds to the size of the smallest vortices in a turbulent flow. This length $L_K$ is calculated in the publication of Kolmogorov (Kolmogorov, A. N., 1941, January, *The local structure of turbulence in incompressible viscous fluid for very large Reynolds numbers*, In Dokl. Akad. Nauk, SSSR, Vol. 30, No. 4, pp. 301-305) and described by the following formula (1):

$$L_k = v^{3/4} \cdot \varepsilon^{-1/4} \qquad (1)$$

wherein v is the kinematic viscosity of the flowing liquid medium and ε is the energy dissipated in the fluid per unit of mass (or rate of energy injection into the fluid).

Zhou et al. (Zhou, G., Kresta, S. M., 1996, *Impact of tank geometry on the maximum turbulence energy dissipation rate for impellers*, AIChE journal, 42(9), 2476-2490) describe the relationship between £ and the geometry of a container wherein a liquid medium is agitated by a blade impeller-type agitator. This relationship is given by the following formula (2):

$$\varepsilon = \frac{N_p \cdot D^5 \cdot N^3}{V} \qquad (2)$$

wherein $N_p$ is the dimensionless power number (or Newton number) of the agitator in the liquid medium, D is the diameter of the agitator (in metre), N is the rotation speed (in number of revolutions per second) and V is the volume of the liquid medium (in cubic metre). This relationship is used for calculating ε corresponding to the geometry of a container and an agitator used for implementing the invention. The power number $N_p$ is given in a known manner by the formula (3):

$$N_p = \frac{P}{N^3 D^5 \rho} \qquad (3)$$

wherein P is the power provided by the agitator, and p is the density of the liquid medium. Formula (3) can be adjusted as described in Nienow et al. (Nienow, A. W., & Miles, D., 1971, *Impeller power numbers in closed vessels*, Industrial & Engineering Chemistry Process Design and Development, 10(1), 41-43) or Zhou et al. (Zhou, G., Kresta, S. M., 1996, *Impact of tank geometry on the maximum turbulence energy dissipation rate for impellers*, AIChE journal, 42(9), 2476-2490) depending on the Reynolds number of the flow of the liquid medium. It is also possible to calculate the Reynolds number of the system by the following formula (4):

$$Re = \frac{N \cdot D^2}{v} \qquad (4)$$

General Architecture of the Fluidic System

Figure 1:
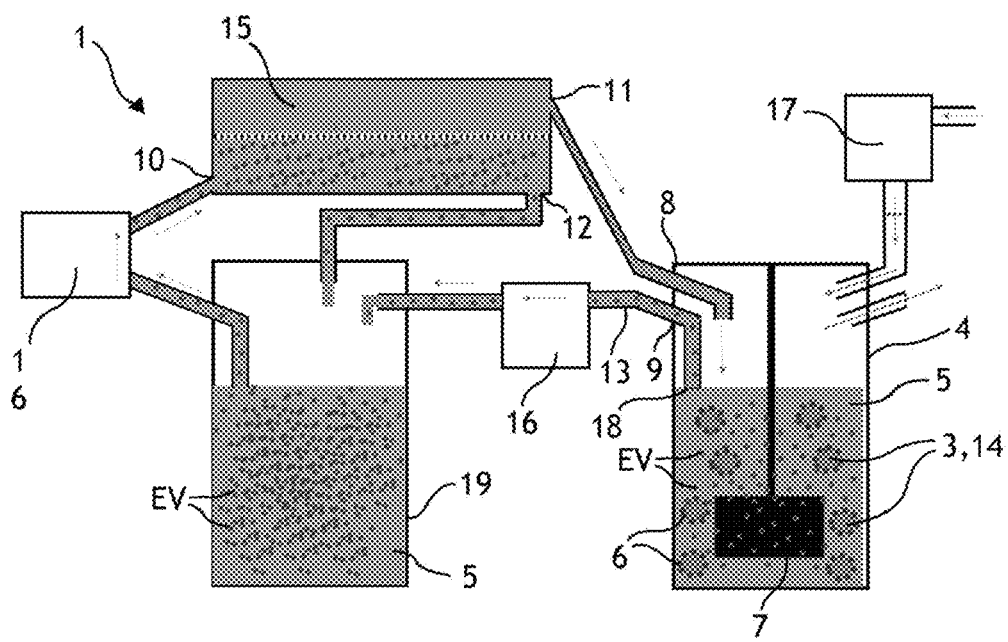
FIG. 1 schematically illustrates a fluidic system for producing extracellular vesicles.

FIG. 1 schematically illustrates a fluidic system 1 for producing extracellular vesicles EV. The fluidic system 1 for producing extracellular vesicles EV aims at producing extracellular vesicles EV in a large amount in a container 4. However, the invention is not limited to this embodiment and may comprise a series of containers 4 that are fluidly connected in parallel or in series.

The container 4 contains a liquid medium 5. The container 4 can be a vessel, a flask, for example made of glass or a plastic material, or any other container adapted to contain a liquid medium 5. The volume of the container 4 is one of the factors allowing to produce extracellular vesicles EV in a large amount: this volume can be comprised between 50 mL and 500 L, preferably between 100 mL and 100 L, and preferably between 500 mL and 10 L. The volume of the container 4 schematically illustrated in FIG. 1 is of 1 L. The container 4 typically comprises a gas input and a gas output, through which can flow an atmosphere comprising $O_2$ and $CO_2$ concentrations adapted for the cell culture, for example comprising 5% of $CO_2$. This atmosphere can come from an adapted gas injector/mixer or from a $CO_2$ controlled atmosphere oven. A second pump 17 allows controlling this gas flow in the container 4. The container 4 also comprises an output 9 capable of comprising liquid medium 5 and extracellular vesicles EV. This output is completed by a means for separating and/or filtering microcarriers 3 allowing not to recover microcarriers 3 out of the container 4. This output 9 allows extracting the produced extracellular vesicles EV from the container 4. The container 4 can also comprise at least one input 8 adapted to introduce the liquid medium 5 into the container 4.

The liquid medium 5 can generally be a saline, for example isotonic solution. Preferably, the liquid medium 5 is a liquid culture medium with or the addition of compounds allowing the culture of the cells of interest, or a medium supplemented with serum previously purified from extracellular vesicles or a medium without serum, allowing not to contaminate the extracellular vesicles EV produced by the fluidic system 1 by proteins or other vesicles from a serum. A DMEM-type liquid medium 5 without serum can be used. The maximum volume of liquid medium 5 is partly determined by the container 4. This maximum volume can also be comprised between 50 mL and 500 L, preferably between 100 mL and 100 L, and more preferably between 500 mL and 10 L. The minimum volume of liquid medium 5 contained in the container 4 is partly determined by the choice of the agitator 7 allowing to agitate the liquid medium 5.

The fluidic system 1 also comprises microcarriers 3 suspended in the liquid medium 5. The microcarriers 3 can be microbeads 14, for example made of Dextran, each microbead 14 being able to be covered with a layer of collagen or other material necessary for the culture of cells. Other materials can be used for the manufacture of microcarriers 3, such as glass, polystyrene, polyacrylamide, collagen and/or alginate. In a general manner, the set of microcarriers adapted for cell culture is adapted for the production of extracellular vesicles EV. For example, the density of the microcarriers 3 can be slightly greater than that of the liquid medium 5. The density of the microbeads 14 made of Dextran is for example of 1.04. This density allows the microbeads 14 to be suspended in the liquid medium 5 by slightly agitating the liquid medium 5, the drag of each microcarrier 3 in the liquid medium 5 being dependant on the density of the microcarrier 3. The maximum size of the microcarriers 3 can be comprised between 50 μm and 500 μm, preferably between 100 μm and 300 μm, and preferably between 130 μm and 210 μm.

For example, the microcarriers 3 can be microbeads 14 of the Cytodex 1 (registered trademark) type. A powder formed by these microbeads 14 can be rehydrated and sterilised before use. 5 g of PBS can be used, then in a culture medium (for example DMEM) without serum, at 4° C. before use.

The fluidic system 1 also comprises producer cells 6. The extracellular vesicles EV are produced by the fluidic system 1 from these producer cells 6. The producer cells 6 can be cultured, before the production of extracellular vesicles EV by the fluidic system 1, on the surface of the microcarriers 3 in an adapted cell culture medium. Thus, no transfer of cells between the culture of the producer cells 6 and the production of the extracellular vesicles EV is necessary, which allows avoiding any contamination and simplifying the whole method. The majority of producer cells 6 are adherent to the surface of the microcarriers 3, even if a minority proportion of producer cells 6 can be detached, for example by agitation of the liquid medium 5. The other producer cells are then suspended in the liquid medium 5 or sedimented at the bottom of the container 4. In a general manner, any type of producer cells 6 can be used, including non-adherent producer cells, and preferably adherent producer cells 6. For example, the producer cells 6 can be multipotent cells, or Induced Pluripotent Stem Cells (IPS or IPSCs). They can also be genetically modified cells and/or tumour lines.

The container 4 also comprises an agitator 7 allowing to agitate the liquid medium 5. The agitator 7 can be a blade impeller, the blades of which are at least partly immersed into the liquid medium 5, and moved by a transmission of magnetic forces. The agitator 7 can also be a liquid medium 5 perfusion system at a flow rate sufficient to agitate the liquid medium 5 contained by the container, or a system with rotating walls (for example arranged on rollers). The agitator 7 and the dimensions of the container 4 are adapted to control a turbulent flow of the liquid medium 5 in the container 4. Turbulent flow means a flow whose Reynolds number is greater than 2000. For example, the Reynolds number can be calculated by formula (4). Preferably, the Reynolds number Re of the liquid medium 5 flow is greater than 7 000, preferentially than 10 000 and preferentially than 12 000.

The agitator 7 used in the exemplary embodiments of the invention comprises a blade impeller arranged in a container 4 and moved by a magnetic force transmission system. The speed of the blade impeller in the liquid medium 5 causes the liquid medium 5 to flow. The agitator is adapted to control a flow, which, taking into account the dimensions of the container 4, is turbulent. In the case of the agitator 7 illustrated in FIG. 1, several parameters allow calculating a value representative of the turbulence of the liquid medium 5, particularly the kinematic viscosity v of the liquid medium 5, the dimensions of the container 4 and particularly the volume V of the liquid medium 5 contained in the container 4, the power number $N_p$ corresponding to the submerged part of the blade impeller, the diameter D of the agitator and particularly of the impeller, the rotation speed N of the impeller. Thus, the user can calculate, according to these parameters, representative values of the turbulence of the flow, and particularly the Kolmogorov length $L_K$, as given by the equations (1), (2) and (3). Particularly, the agitator 7 is adapted to control a flow wherein the length $L_K$ is less than or equal to 75 μm and preferably to 50 μm.

In an exemplary embodiment of the fluidic system 1, the rotation speed of the agitator 7 is capable of being controlled at 100 rpm (rotations per minute), the diameter of a blade impeller is of 10.8 cm and the volume of the liquid medium contained in the container 4 is of 400 mL. The power number $N_P$ of the blade impeller in the liquid medium 5, measured by formula (3), is substantially equal to 3.2. The energy dissipated per unit of mass £, calculated, by formula (2), is equal to $5.44 \times 10^{-1}$ J·kg$^{-1}$. The Kolmogorov length $L_K$ calculated by formula (1) is thus equal to 41.8 μm.

Preparation of Microcarriers and Producer Cells

The container 4 can be a single use container or sterilised before any introduction of liquid medium 5, microcarriers 3 and producer cells 6. The microcarriers 3, in this case microbeads 14, are also sterilised. The microbeads 14 are incubated in the culture medium of the producer cells 6, comprising serum, in the container 4. This incubation allows oxygenating the culture medium and covering the surface of the microbeads 14 with an at least partial layer of proteins, promoting the adhesion of the producer cells 6 to the surface of the microbeads 14.

The producer cells 6, before being introduced into the fluidic system 1, are suspended by means of a medium comprising trypsin. Then, they can be centrifuged at 300 G for five minutes to be concentrated in the bottom of a tube, so as to replace the medium comprising trypsin with a DMEM medium. The producer cells 6 are then introduced into the container 5, comprising the culture medium and the microbeads 14, in an amount corresponding substantially to 5 to 20 producer cells 6 per microbead 14. Thereafter, the producer cells 6 and the microbeads 14 are agitated then sedimented, so as to bring the microbeads 14 into contact with the producer cells 6, and promote the adhesion of the producer cells 6 on the surface of the microbeads 14. The agitation can resume periodically, so as to promote the homogeneity of the adhesion of the producer cells 6 to the surface of the microbeads 14, for example every 45 minutes for 5 to 24 hours. Thereafter, the culture of the producer cells is carried out with a weak agitation of the culture medium (for example the rotation of a blade impeller at a speed of 20 rpm), as well as a regular replacement of the culture medium (for example a replacement of 5% to 40% of the culture medium each day).

Example of Production of Extracellular Vesicles EV

The extracellular vesicles EV are produced in a container 4 containing a liquid medium 5, for example without serum, microcarriers 3 and producer cells 6 adhering to the surface of the microcarriers 3. The medium used before production for the culture of producer cells 6 on the microcarriers 3 comprising serum, the container 4 is washed three to four times with a DMEM liquid medium 5 without serum, each washing corresponding for example to a volume of about 400 mL. The agitation of the liquid medium 5 is then controlled by the agitator 7 so as to cause a turbulent flow in the container 4. The agitation is preferably adjusted so as to control a flow of the liquid medium 5 wherein the Kolmogorov length $L_K$ is less than or equal to 75 μm and preferably to 50 μm. The agitation of the liquid medium 5 is controlled at least for half an hour, preferably for more than one hour, and preferably for more than two hours. The production of extracellular vesicles EV can be measured during production. To this end, the agitation can be temporarily interrupted. The microbeads 14 are allowed to sediment at the bottom of the container 4, then a sample of liquid medium 5 comprising extracellular vesicles EV is taken. The sample is centrifuged at 2000 G for 10 minutes, so as to remove the cellular debris. The supernatant is analysed by an individual particle tracking method (or NTA, acronym for Nanoparticle Tracking Analysis) so as to count the number of extracellular vesicles EV and to deduce the concentration of extracellular vesicles EV of the samples. One can verify that the concentration of extracellular vesicles EV at the beginning of the agitation is close to zero or negligible.

The extracellular vesicles EV produced can also be observed and/or counted by transmission electron cryomicroscopy. To this end, a drop of 2.7 μL of solution comprising extracellular vesicles EV is deposited on a grid adapted for cryomicroscopy, then immersed in liquid ethane, causing said drop to be almost instantaneously frozen, avoiding the formation of ice crystals. The grid carrying the extracellular vesicles EV is introduced into the microscope and the extracellular vesicles EV are observed at a temperature of the order of −170° C.

Separation of Extracellular Vesicles

The extracellular vesicles EV produced in the container 4 can be extracted from the container 4 through the container 4 output 9, suspended in liquid medium 5. A filter 18 can be arranged at the output 9 so as to filter the microcarriers 3 and the producer cells 6 adhering to the microcarriers 3 during the extraction of the extracellular vesicles EV from the container 4. A connector 13 is fluidly connected to the output 9, allowing the transport of the liquid medium 5 comprising the produced extracellular vesicles EV.

The fluidic system 1 can comprise a separator 15 of extracellular vesicles EV. The separator 15 comprises a separator input 10, wherein the liquid medium 5 comprising extracellular vesicles EV from the container 4 can be directly or indirectly conveyed. The separator 15 may also comprise a first separator output 11, through which the liquid medium 5 is capable of leaving the separator 15 with a concentration of extracellular vesicles EV which is lower than at the separator 15 input 10, or even substantially zero. The separator 15 can also comprise a second separator 15 output 12, from which the liquid medium 5 is capable of leaving the separator 15 with a concentration of extracellular vesicles EV which is greater than at the separator 15 input 10.

In a general manner, the separator 15 of the extracellular vesicles EV can be fluidly connected to the container 4 so as to be capable of reintroducing a liquid medium 5 depleted of vesicles EV into the container 4, for example through the input 8 of the container 4. Thus, the production and/or extraction of extracellular vesicles EV can be carried out continuously, at a substantially constant volume of liquid medium 5 in the container 4.

In the exemplary embodiment of a fluidic system 1 illustrated in FIG. 1, the liquid medium 5 can be extracted from the container 4 by a first pump 16, via a connector 13, so as to transport the liquid medium 5 in a collector 19. Another first pump 16 allows conveying the liquid medium 5 contained in the collector 19 to the separator 15 input 10, via another connector. The first separator 15 output 11 is connected to the container 4 via a connector, so as to reintroduce liquid medium 5 depleted of extracellular vesicles EV into the container 4. The second separator 15 output 12 is connected to the collector 19 via a connector, so as to enrich the liquid medium 5 contained in the collector 19 with extracellular vesicles EV. Alternatively, the separator 15 input 10 can be directly connected to the container 4 output 9 (or via a first pump 16). The first separator 15 output 11 is connected to the container 4 and the second separator 15 output 12 is connected to the collector 19. Several separators can also be disposed in series to vary the degree of extracellular vesicle EV separation in the liquid medium 5, and/or in parallel to adapt the liquid medium 5 flow rate in each separator 15 to the flow rate of a first pump 16.

Influence of Agitation on the Production of Extracellular Vesicles EV

Figure 2:
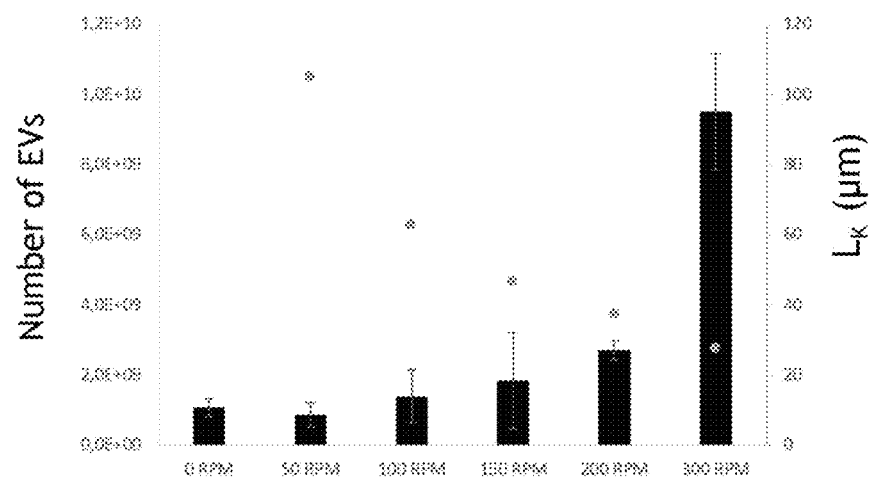
FIG. 2 illustrates the number of extracellular vesicles produced by HUVEC cells in a fluidic system for different agitations.

FIG. 2 illustrates the number of extracellular vesicles EV produced in a fluidic system 1 for different agitations controlled by the agitator 7. The left ordinate corresponds to the numbers of extracellular vesicles EV produced in the container 4. Each column corresponds to a production of extracellular vesicles EV for different rotation speeds of the agitator 7 in the container 4. The right ordinate corresponds to the length $L_K$ caused by the agitator 7 during the production of extracellular vesicles EV, calculated by the formulae (1), (2) and (3). The extracellular vesicles EV are produced from HUVEC-type producer cells 6 in the container 4 using a concentration of 3 g·L$^{-1}$ of microcarriers 3 in 50 mL of liquid medium 5 in a 100 ml spinner flask. A significantly high production of extracellular vesicles EV can be observed by controlling a flow of liquid medium 5 wherein the length $L_K$ is equal to 35 μm (production corresponding to the column 300 RPM) compared to the production of extracellular vesicles EV under conditions of weaker agitation wherein the length $L_K$ is equal to 75 μm and preferably to 50 μm (production corresponding to the column 150 RPM).

Figure 3:
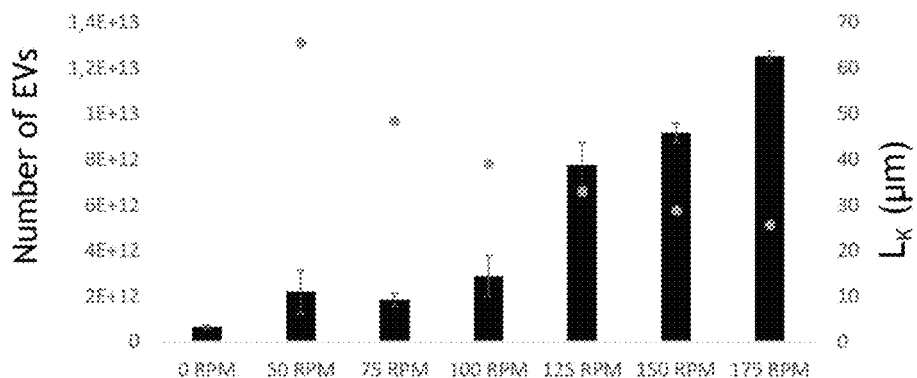
FIG. 3 illustrates the number of extracellular vesicles produced by HUVEC cells in a fluidic system for different agitations.

FIG. 3 illustrates the number of extracellular vesicles EV produced in a fluidic system 1 for different agitations controlled by the agitator 7. Twenty million HUVEC-type producer cells 6 are used, using a concentration of 3 g·L$^{-1}$ of microcarriers 3 in 350 mL of liquid medium 5 in a 1000 mL spinner flask. The left ordinate corresponds to the numbers of extracellular vesicles EV produced in the container 4. Each column corresponds to a production of extracellular vesicles EV for different rotation speeds of the agitator 7 in the container 4. The right ordinate corresponds to the length $L_K$ caused during the production of extracellular vesicles EV, calculated by the formulae (1), (2) and (3). A significantly high production of extracellular vesicles EV can be observed by controlling a flow of liquid medium 5 wherein the length $L_K$ is less than 40 µm compared to the production of extracellular vesicles EV under conditions of weaker agitation (production corresponding to the columns 125 RPM, 150 RPM and 175 RPM).

Figure 4:
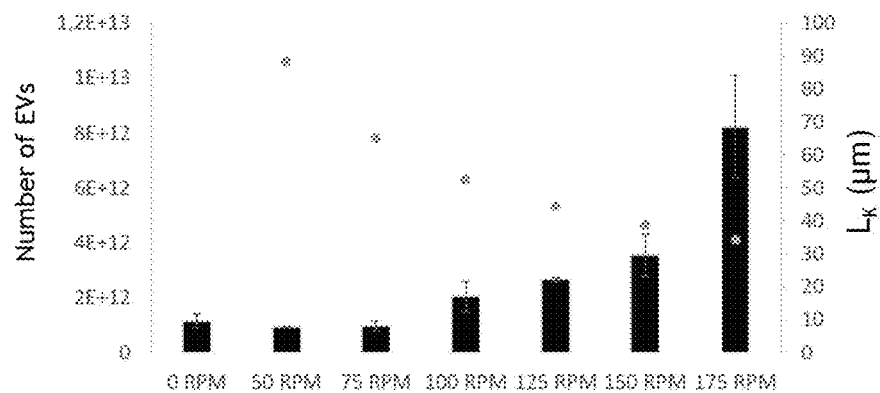
FIG. 4 illustrates the number of extracellular vesicles produced by MSC cells in a fluidic system for different agitations.

FIG. 4 illustrates the number of extracellular vesicles EV produced in a fluidic system 1 for different agitations controlled by the agitator 7. Producer cells 6 of the MSC type (acronym for mesenchymal stem cell) are used, and microcarriers 3 are introduced at a concentration of 3 g·L$^{-1}$ in 200 mL of liquid medium 5 in a 500 mL spinner flask. The left ordinate corresponds to the numbers of extracellular vesicles EV produced in the container 4. Each column corresponds to a production of extracellular vesicles EV for different rotation speeds of the agitator 7 in the container 4. The right ordinate corresponds to the length $L_K$ caused during the production of extracellular vesicles EV, calculated by the formulae (1), (2) and (3). A significantly high production of extracellular vesicles EV can be observed by controlling a flow of liquid medium 5 wherein the length $L_K$ is equal to 35 µm (production corresponding to the column 175 RPM), compared to the production of extracellular vesicles EV under conditions of weaker agitation wherein the length $L_K$ is equal to 50 µm.

Figure 5:
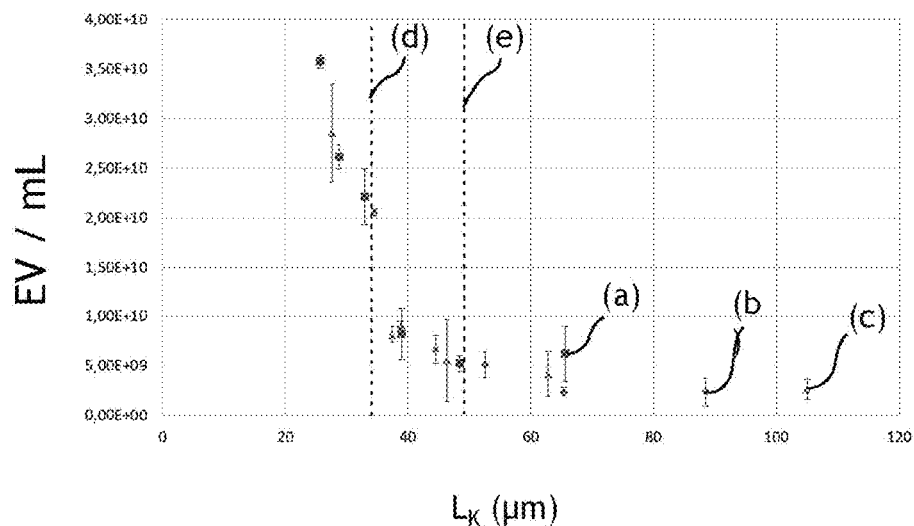
FIG. 5 illustrates the influence of the Kolmogorov length on the number of extracellular vesicles produced by HUVEC and MSC cells.

FIG. 5 illustrates the influence of the Kolmogorov length $L_K$ on the number of produced extracellular vesicles EV. The length $L_K$ is a scale parameter concerning the production of the extracellular vesicles EV. The squares (a) correspond to the productions of extracellular vesicles EV illustrated in FIG. 2 for different lengths $L_K$, the diamonds (b) correspond to the productions of extracellular vesicles EV illustrated in FIG. 3 for different lengths $L_K$ and the triangles (c) correspond to the productions of extracellular vesicles EV illustrated in FIG. 4 for different lengths $L_K$. A characteristic value of $L_K$ characterising the change in slope of the production of extracellular vesicles EV as a function of $L_K$ can be extracted from the diagram of FIG. 5, substantially equal to $L_K$=50 µm. Thus, for $L_K$ values less than or equal to 50 µm, the production of extracellular vesicles EV increases significantly.

Figures 6, 7:
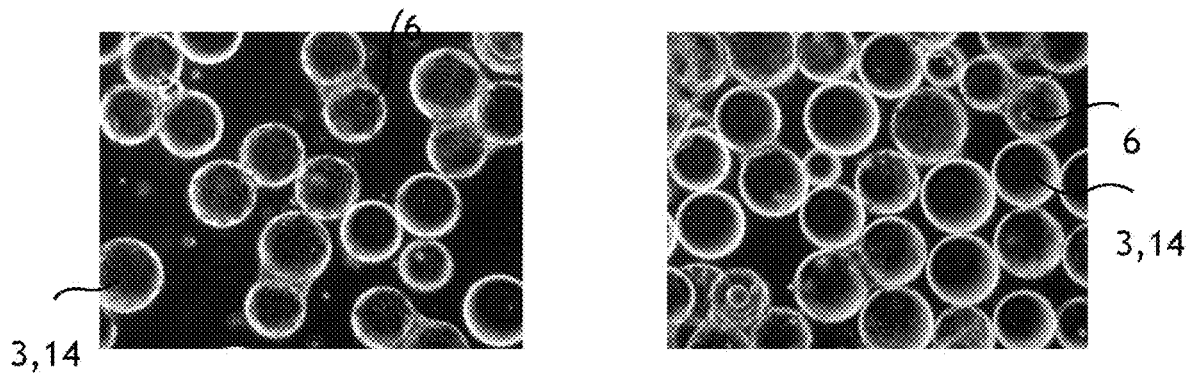
FIG. 6 illustrates producer cells adhering on the surface of microcarriers.
FIG. 7 illustrates producer cells adhering on the surface of microcarriers.

FIG. 6 illustrates producer cells 6 adhering on the surface of the microcarriers 3, in this case of the microbeads 14, suspended in the liquid medium 5, before the agitation corresponding to a production of extracellular vesicles EV. Producer cells 6 adhering to the surface of the microcarriers 3 are visible and quantifiable.

FIG. 7 illustrates producer cells 6 adhering on the surface of the microcarriers 3, in this case of the microbeads 14, suspended in the liquid medium 5, after the agitation corresponding to a production of extracellular vesicles EV. Producer cells 6 adhering to the surface of the microcarriers 3 are visible and quantifiable. The comparison between the number of producer cells adhering to the surface of the microcarriers 3 before and after the agitation for the production of extracellular vesicles EV allows verifying that the agitation conditions previously described, for example an agitation causing a flow wherein the length $L_K$ is less than 75 µm and preferably than 50 µm, do not cause the detachment of the producer cells 6 from the microcarriers 3.

Figure 8:
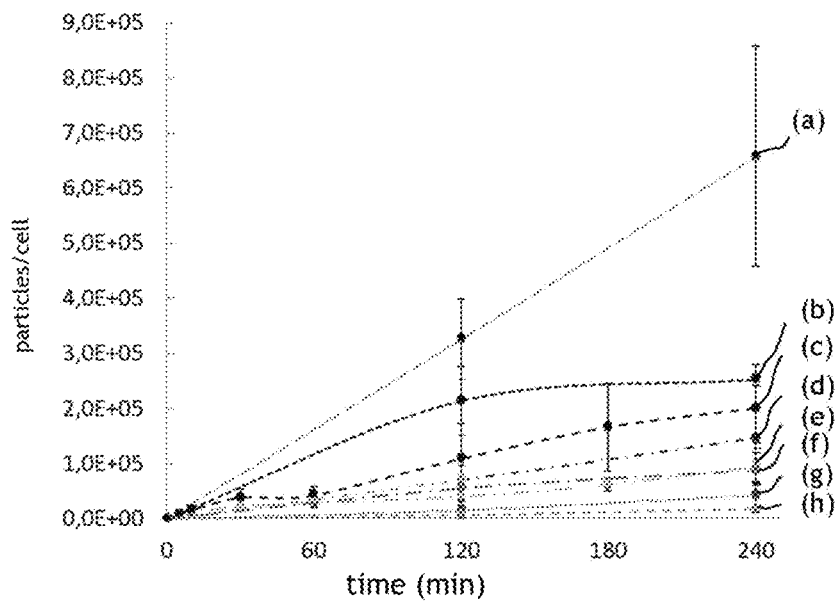
FIG. 8 illustrates the production yield of extracellular vesicles for different durations of agitation, for different producer cells and for different conditions of agitation.

FIG. 8 illustrates the production yield of extracellular vesicles EV for different durations of agitation, for different producer cells, and for different agitation conditions, corresponding to different lengths $L_K$ of the flow controlled by the agitator 7. The curve (a) illustrates the evolution, during agitation, of the ratio between the number of produced particles (including extracellular vesicles EV) and between the number of producer cells 6 introduced into the container 4, the producer cells 6 being of the murine MSC type, and the flow of the liquid medium 5 being characterised by a length $L_K$ substantially equal to 35 µm. The curve (b) illustrates the same evolution, the producer cells 6 being of the human MSC type, and the flow of the liquid medium 5 being characterised by a length $L_K$ substantially equal to 33 µm. The curve (c) illustrates the same evolution, the producer cells 6 being of the HUVEC type, and the flow of the liquid medium 5 being characterised by a length $L_K$ substantially equal to 35 µm. The curve (d) illustrates the same evolution, the producer cells 6 being of the human MSC type, and the flow of the liquid medium 5 being characterised by a length $L_K$ substantially equal to 35 µm. The curve (e) illustrates the same evolution, the producer cells being of the HUVEC type, and the flow of the liquid medium 5 being characterised by a length $L_K$ substantially equal to 50 µm. The curve (f) illustrates the same evolution, the producer cells being of the murine MSC type, and the flow of the liquid medium 5 being characterised by a length $L_K$ substantially equal to 50 µm. The curve (g) illustrates the same evolution, the producer cells 6 being of the human MSC type, and the flow of the liquid medium 5 being characterised by a length $L_K$ substantially equal to 50 µm. The curve (h) illustrates the same evolution, the producer cells being of the murine MSC type, and the flow of the liquid medium 5 being characterised by a length $L_K$ substantially equal to 53 µm. Thus, the extracellular vesicles EV are produced at yields higher than those known, for a duration of agitation greater than half an hour.

Figure 9:
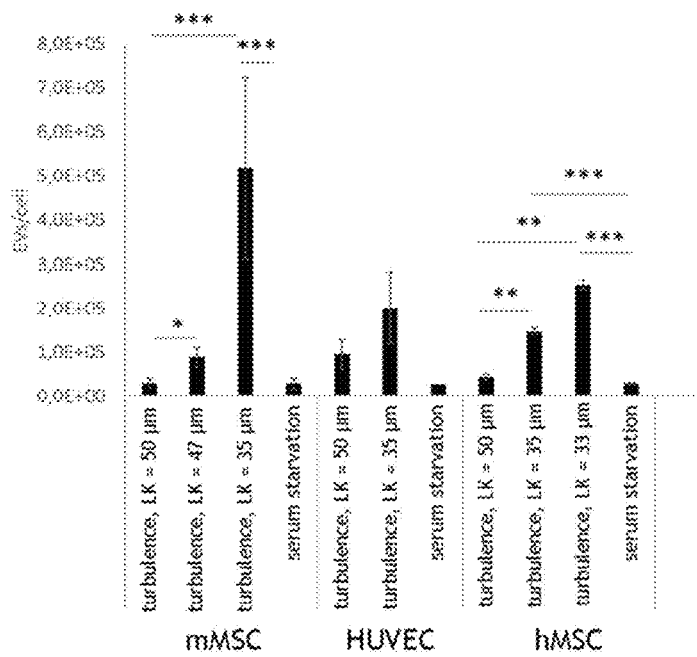
FIG. 9 illustrates the production yield of extracellular vesicles for different producer cells, and for different agitation conditions, after 240 minutes of agitation in comparison with the serum deprivation method for 72 h.

FIG. 9 illustrates the production yield of extracellular vesicles EV for different producer cells 6, and for different agitation conditions, after 240 minutes of agitation. The four left columns illustrate the production yield of extracellular vesicles EV using murine MSC-type producer cells 6. The production yield for three agitation conditions, corresponding to an agitation resulting in a length $L_K$ of 50 µm (first column), 47 µm (second column) and 35 µm (third column) is compared to the production yield according to the serum starvation method (or serum deprivation method). The production yield of extracellular vesicles EV under the conditions $L_K$=47 µm and $L_K$=35 µm is significantly higher than under the $L_K$=50 µm and serum starvation conditions. Three columns illustrate the production yield of extracellular vesicles EV using HUVEC-type producer cells 6. The production yield for two agitation conditions, corresponding to an agitation resulting in a length $L_K$ of 50 µm (fourth column) and 47 µm (fifth column) is compared to the production yield according to the serum starvation method. The production yield of extracellular vesicles EV under the condition $L_K$=35 µm is higher than under the $L_K$=50 µm and serum starvation conditions. The four rightmost columns of the figure illustrate the production yield of extracellular vesicles EV using human MSC-type producer cells 6. The production yield for three agitation conditions, corresponding to an agitation resulting in a length $L_K$ of 50 µm (eighth column), 35 µm (ninth column) and 33 µm (tenth column) is compared to the production yield according to the serum starvation method. The production yield of extracellular vesicles EV under the conditions $L_K$=35 μm and $L_K$=33 μm is significantly higher than under the $L_K$=50 μm and serum starvation conditions.

Figure 10:
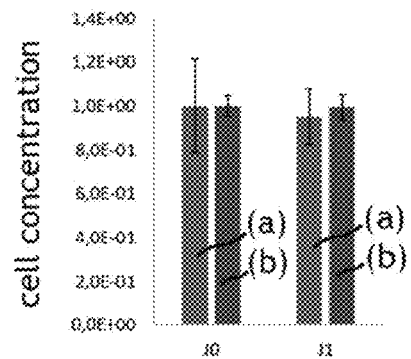
FIG. 10 illustrates the concentration of producer cells adhering on the microcarriers before and after agitation, for different conditions of agitation.

FIG. 10 illustrates the concentration of producer cells 6 adhering on the microcarriers 3 before and after agitation, for different agitation conditions. Columns (a) correspond to the concentration of producer cells 6 before an agitation (J0) for the production of extracellular vesicles EV and one day after the agitation (J1), under agitation conditions called "strong" agitation conditions, that is to say when the agitator 7 is controlled to cause a flow characterised by a length $L_K$=35 μm. Columns (b) correspond to the concentration of producer cells 6 before an agitation (J0) for the production of extracellular vesicles EV and one day after the agitation (J1), under agitation conditions called "weak" agitation conditions, that is to say when the agitator 7 is controlled to cause a flow characterised by a length $L_K$=50 μm. No significant decrease in the concentration of producer cells 6 can be observed after the agitation of the liquid medium 5 for the production of extracellular vesicles EV.

Figure 11:
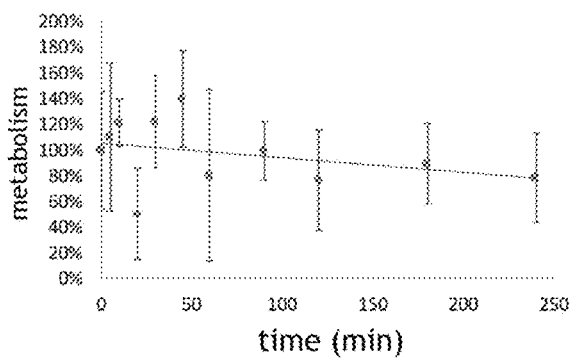
FIG. 11 illustrates the metabolism of HUVEC-type producer cells under agitation conditions for the production of extracellular vesicles.

FIG. 11 illustrates the metabolic activity of the HUVEC-type producer cells 6 under agitation conditions for producing extracellular vesicles EV. The agitation of the liquid medium 5 is controlled by an agitator 7 rotating at 75 RPM, in a 1 L spinner flask, causing a flow characterised by a length $L_K$ substantially equal to 50 μm, for 240 minutes. The metabolism is measured by observing the variation in the wavelength emitted by the Alamar blue reagent in the liquid medium 5. No significant drop in the metabolism of the producer cells 6 can be observed under these agitation conditions.

Figure 12:
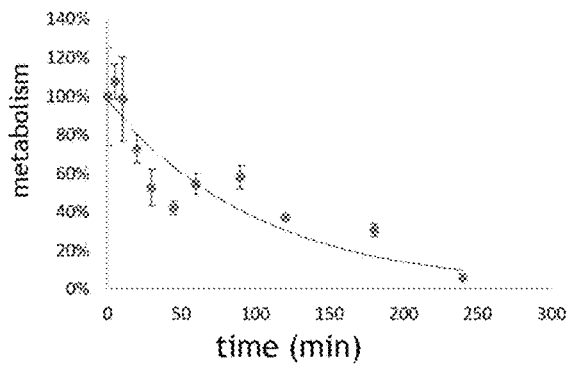
FIG. 12 illustrates the metabolism of HUVEC-type producer cells under agitation conditions for the production of extracellular vesicles.

FIG. 12 illustrates the metabolism of the HUVEC-type producer cells 6 under agitation conditions for producing extracellular vesicles EV. The agitation of the liquid medium 5 is controlled by an agitator 7 rotating at 125 RPM in a 1 L spinner flask, causing a flow characterised by a length $L_K$ substantially equal to 35 μm for 240 minutes. The metabolism is measured by observing the variation in the wavelength emitted by the Alamar blue reagent in the liquid medium 5. A drop, or even a disappearance of the metabolism of the producer cells 6 can be observed after 250 minutes of agitation. However, this decrease in cell metabolism does not prevent the production of extracellular vesicles EV during agitation.

Figure 13:
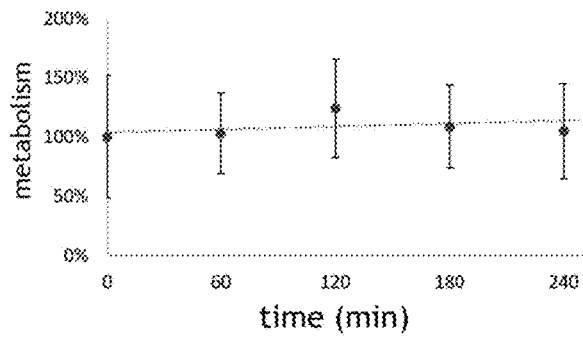
FIG. 13 illustrates the metabolism of murine MSC-type producer cells under agitation conditions for the production of extracellular vesicles EV.

FIG. 13 illustrates the metabolism of MSC-type producer cells 6 under agitation conditions for producing extracellular vesicles EV. The agitation of the liquid medium 5 is controlled by an agitator 7 rotating at 75 RPM in a 1 L spinner flask, causing a flow characterised by a length $L_K$ substantially equal to 50 μm, for 240 minutes. The metabolism is measured by observing the variation in the wavelength emitted by the Alamar blue reagent in the liquid medium 5. No significant drop in the metabolism of the producer cells 6 can be observed under these agitation conditions.

Figure 14:
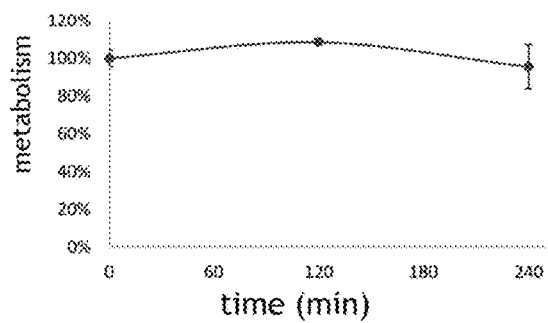
FIG. 14 illustrates the metabolism of murine MSC-type producer cells under agitation conditions for the production of extracellular vesicles.

FIG. 14 illustrates the metabolism of MSC-type producer cells 6 under agitation conditions for producing extracellular vesicles EV. The agitation of the liquid medium 5 is controlled by an agitator 7 rotating at 125 RPM in a 1 L spinner flask, causing a flow characterised by a length $L_K$ substantially equal to 35 μm for 240 minutes. The metabolism is measured by observing the variation in the wavelength emitted by the Alamar blue reagent in the liquid medium 5. No significant drop in the metabolism of the producer cells 6 can be observed under these agitation conditions.

Thus, the weak agitation conditions, corresponding to an agitation causing a flow characterised by a length $L_K$ substantially equal to 50 μm, allow reusing the producer cells 6 for the production of subsequent extracellular vesicles EV.

Figure 15:
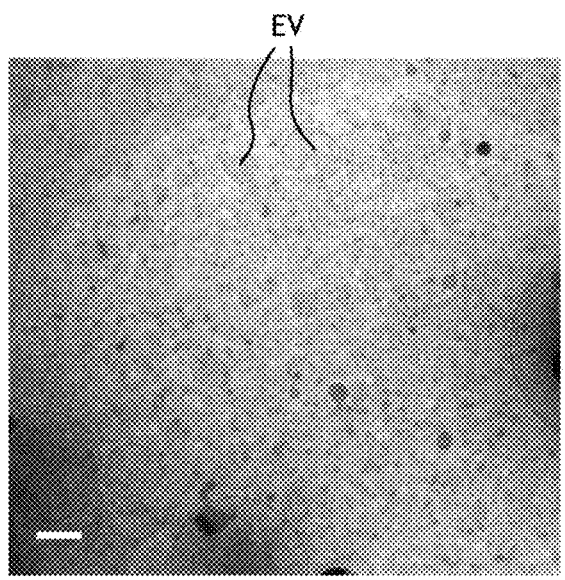
FIG. 15 is a cryo-electron microscopy photomicrograph of extracellular vesicles produced by a fluidic system.

FIG. 15 is a photomicrograph of extracellular vesicles EV produced by murine MSC cells by a fluidic system 1. The scale bar corresponds to a length of 200 nm. The microphotography is performed using the technique of transmission electron cryomicroscopy (cryo-TEM).

Figure 16:
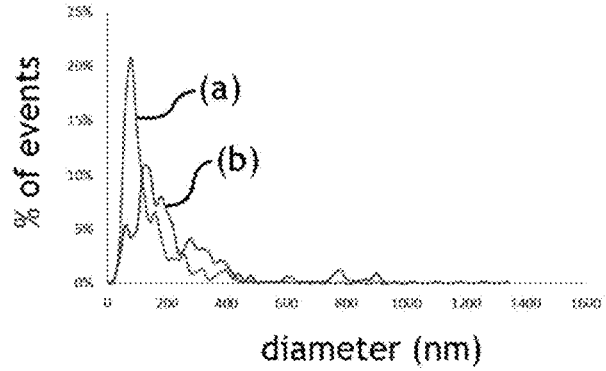
FIG. 16 illustrates the distribution of the diameter of extracellular vesicles produced by the fluidic system.

FIG. 16 illustrates the distribution of the diameter of the extracellular vesicles EV produced by the fluidic system 1 measured by cryo-TEM. The distribution (a) corresponds to extracellular vesicles EV produced by murine MSC cells with an agitation causing a flow characterised by a length $L_K$ substantially equal to 35 μm (strong agitation condition). The distribution (b) corresponds to extracellular vesicles EV produced with an agitation causing a flow characterised by a length $L_K$ substantially equal to 50 μm (weak agitation condition). The median diameter of the extracellular vesicles EV produced under weak agitation conditions is greater than the median diameter of the extracellular vesicles EV produced under strong agitation conditions. The size of the extracellular vesicles EV can be substantially comprised between 30 and 500 nm.

FIG. 17 illustrates the purity of the extracellular vesicles EV produced by the fluidic system 1 in the liquid medium 5 indicated by the ratio between the number of particles and the mass of proteins in micrograms. During the production of extracellular vesicles EV, different entities can be produced by the producer cells 6, in this case extracellular vesicles EV but also protein aggregates. The quantification of particles by analysis of individual particle tracking (or NTA for Nanoparticle Tracking Analysis) does not allow differentiating these different entities: also, it is advantageous to quantify the ratio between the number of particles measured by NTA and the mass of produced proteins, defining the purity in extracellular vesicles EV. Columns (a) illustrated in FIG. 17 correspond to a production of extracellular vesicles EV from murine MSC-type producer cells 6, and columns (b) correspond to a production of extracellular vesicles EV from human MSC-type producer cells 6. The two left columns correspond to a production of extracellular vesicles EV under strong agitation conditions, and the two right columns correspond to a production of extracellular vesicles EV according to the serum starvation method. The purity in extracellular vesicles EV of the medium obtained after production is comparable in both methods.

FIG. 18 illustrates the pro-angiogenic properties of a liquid medium without serum 5 comprising extracellular vesicles EV produced by murine MSC cells by the fluidic system 1. Panel A of FIG. 18 is a photograph of a surface on which HUVEC-type cells are adherent. Cells have been removed from part of the surface (area without cells in the middle of the photograph). This photograph is taken at the beginning of an experiment, at time t=0 h, during which the cells are covered with a liquid medium 5 comprising extracellular vesicles EV produced by the fluidic system 1. Panel B of FIG. 18 is a photograph of the same surface, after 4 hours of incubation in the liquid medium 5 comprising the extracellular vesicles EV. Panel C of FIG. 18 is a photograph of the same surface, after 9 hours of incubation in the liquid medium 5 comprising the extracellular vesicles EV. During the experiment, HUVEC-type cells cover the part of the surface on which no cell was present at the beginning of the experiment. Thus, the liquid medium 5 comprising the extracellular vesicles EV has pro-angiogenic and/or pro-proliferative properties.

FIG. 19 illustrates the pro-angiogenic properties of a liquid medium 5 comprising extracellular vesicles EV produced by murine MSC cells by the fluidic system 1 under different conditions. Each column illustrates the normalised percentage of the closure of the margins between 0 h (corresponding to panel A of FIG. 18) and 9 h (corresponding to panel C of FIG. 18) for each incubation condition. The first column ("complete medium") corresponds to an incubation in a HUVEC cell culture medium (corresponding to a positive control). The second column ("neg ctrl") corresponds to an incubation in a liquid medium 5 (culture medium) without extracellular vesicles EV, without serum where a given volume of PBS was added. The third column ("strong agitation 10/1") corresponds to an incubation in a liquid culture medium 5 where the same given volume of PBS was added comprising extracellular vesicles EV produced by a fluidic system 1 under strong agitation conditions, wherein the amount of introduced producer cells 6 corresponds to 10 murine MSC producer cells 6 for one receiver HUVEC cell. The fourth column ("weak agitation 10/1") corresponds to an incubation in a culture medium 5 where the same given volume of PBS was added comprising extracellular vesicles EV produced by a fluidic system 1 under weak agitation conditions, wherein the amount of introduced producer cells 6 corresponds to 10 murine MSC producer cells 6 for one receiver HUVEC cell. The fifth column ("lib 10/1") corresponds to an incubation in a HUVEC cell culture medium, depleted of exosomes, the amount of introduced producer cells 6 corresponding to 10 producer cells 6 for one receiver HUVEC cell. The sixth column ("stress 10/1") corresponds to an incubation in a liquid culture medium 5 where the same given volume of PBS was added comprising extracellular vesicles EV produced by serum starvation, the amount of introduced producer cells 6 corresponding to 10 murine MSC producer cells 6 for one receiver HUVEC cell. An incubation in a liquid medium 5 comprising extracellular vesicles EV produced under strong agitation conditions ("strong agitation 10/1") allows significantly covering the part initially devoid of cells.

FIG. 20 illustrates the proliferation of cardiomyocytes after one day of incubation in different liquid media, measured by alamar blue comprised in the incubation medium. The first column corresponds to an incubation in a medium adapted for the culture of H9C2 cardiomyocytes ("complete medium", positive control). The second column corresponds to an incubation in PBS. The third column corresponds to an incubation in a liquid medium 5 comprising extracellular vesicles EV produced by a fluidic system 1 under strong agitation conditions ("strong agitation 10/1"), the amount of introduced producer cells 6 corresponding to 10 producer cells 6 for one receiver cell. The fourth column corresponds to an incubation in a liquid medium 5 comprising extracellular vesicles EV produced by a fluidic system 1 under weak agitation conditions ("weak agitation 10/1"), the amount of introduced producer cells 6 corresponding to 10 producer cells 6 for one receiver cell. The fifth column corresponds to an incubation in a cardiomyocyte culture medium, depleted of exosomes ("lib 10/1"), the amount of introduced producer cells 6 corresponding to 10 producer cells 6 for one receiver cell. The sixth column corresponds to an incubation in a liquid medium 5 comprising extracellular vesicles EV produced by a production method in a medium without serum "stress", the amount of introduced producer cells 6 corresponding to 10 producer cells 6 for one receiver cell. The conditions of incubation in a liquid medium 5 comprising extracellular vesicles EV produced in a fluidic system 1 under strong agitation and/or weak agitation conditions result in a significantly higher proliferation of cardiomyocytes compared to the conditions of incubation in PBS, and under "exo" and "stress" conditions.

Figure 21:
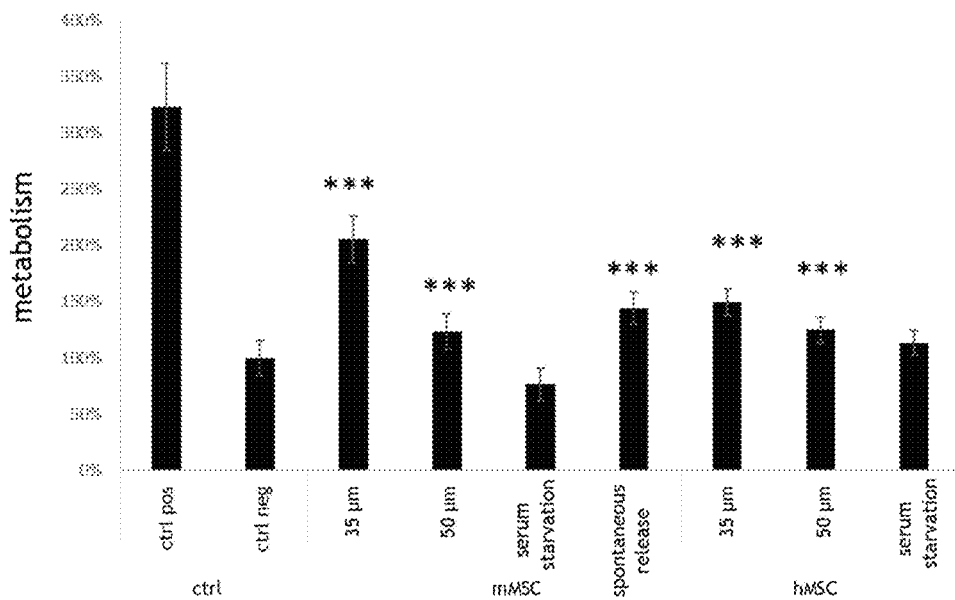
FIG. 21 illustrates the metabolic activity of cardiomyocytes (line H9C2) after two days of incubation in different culture media comprising extracellular vesicles produced by the fluidic system.

FIG. 21 illustrates the proliferation of H9C2 cardiomyocytes after two days of incubation. Cardiomyocytes incubated in a liquid medium 5 comprising extracellular vesicles EV produced from murine MSC-type producer cells 6 by a fluidic system 1 under weak agitation conditions, under strong agitation conditions, as well as by spontaneous release in a complete medium depleted of exosomes, proliferate more significantly than cardiomyocytes incubated in a medium having a serum starvation. Cardiomyocytes incubated in a liquid medium 5 comprising extracellular vesicles EV produced under weak agitation conditions and under strong agitation conditions proliferate more significantly than cardiomyocytes incubated in a medium having a serum starvation.

Figure 22:
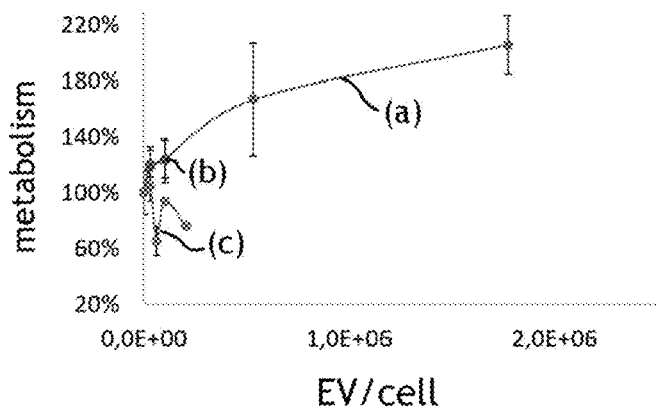
FIG. 22 illustrates the dose effect of an incubation of a liquid culture medium comprising a variable concentration of extracellular vesicles produced by a fluidic system on the proliferation of cardiomyocytes.

FIG. 22 illustrates the dose effect on the proliferation of H9C2 cardiomyocytes of a liquid medium 5 incubation comprising a variable concentration of extracellular vesicles EV produced by a fluidic system 1. The metabolic activity of cardiomyocytes is measured after two days of incubation in a liquid medium by alamar blue. The cardiomyocyte metabolism is measured for three conditions of incubation: in a liquid medium 5 comprising extracellular vesicles EV produced under weak agitation conditions in (a), under weak agitation conditions in (b) and in a liquid medium having a serum starvation in (c). The measurement of cardiomyocyte metabolism is performed, in curves (a) and (b), for different ratios between the concentration of extracellular vesicles EV and the concentration of cardiomyocytes, shown on the abscissa. The curve (a) illustrates the dose effect of the proliferation in the presence of extracellular vesicles EV: the metabolism of cardiomyocytes increases when the ratio of the concentrations between extracellular vesicles EV and cardiomyocytes increases.

Figure 23:
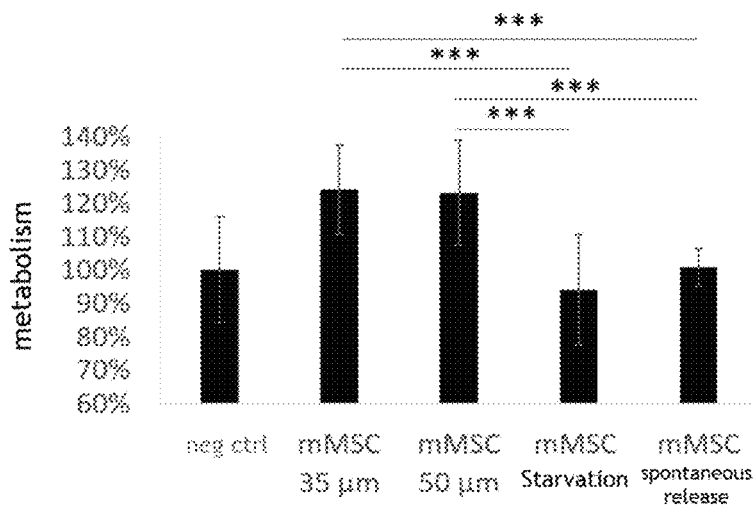
FIG. 23 illustrates the proliferation of cardiomyocytes (line H9C2) after two days of incubation in the presence of a liquid culture medium comprising extracellular vesicles.

FIG. 23 illustrates the proliferation of cardiomyocytes after two days of incubation in the presence of a liquid medium 5 comprising extracellular vesicles EV of murine MSC cells at a concentration of 100 000 extracellular vesicles EV per cardiomyocyte. The proliferation of cardiomyocytes after two days is significantly higher when the liquid incubation medium 5 comprises extracellular vesicles EV produced by a fluidic system 1 under strong agitation or weak agitation conditions, compared to a liquid medium comprising extracellular vesicles EV obtained by serum starvation and/or to a cardiomyocyte culture medium containing extracellular vesicles EV obtained by spontaneous release in a complete medium depleted of exosomes.

Figure 24:
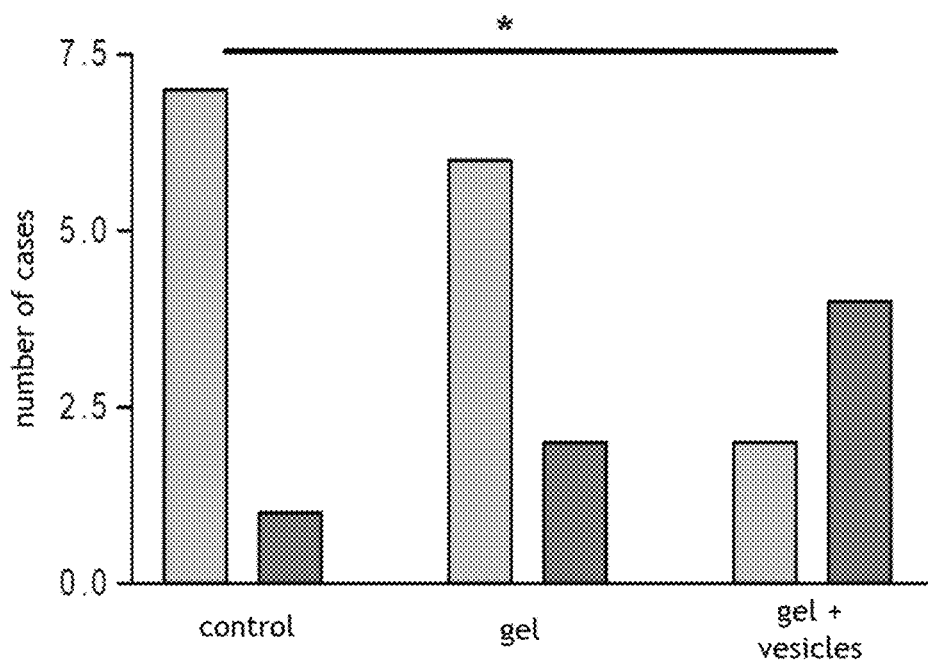
FIG. 24 illustrates the use of a composition of extracellular vesicles produced by the fluidic system as a pharmaceutical composition in a poloxamer gel for the treatment of fistula between the can and the caecum in rats.

FIG. 24 illustrates the use of a composition of extracellular vesicles EV produced by the fluidic system 1 as a pharmaceutical composition. A caecostomy is performed on each rat of a group of rats. The presence of feces is observed at the opening of a fistula formed by the caecostomy, under three conditions: a control condition, a condition corresponding to treatment by the application of a gel comprising poloxamer 407 on the opening of the fistula of each mouse ("gel") and a condition corresponding to the application of this gel comprising extracellular vesicles EV produced by a fluidic system 1 according to a method object of the invention, for example under strong agitation conditions ("gel+ vesicles"). The light grey columns correspond to the fistula openings with feces and the dark grey columns correspond to the fistula openings without feces. The application of a gel comprising extracellular vesicles EV allows significantly reducing the presence of feces at the opening of the fistula under these conditions and results in a reduction in the cases of productive fistulas (which release intestinal secretions) compared to the groups of control and gel without vesicles. Thus, the composition of extracellular vesicles EV produced by the fluidic system 1 can be used in regenerative medicine.

Figure 25:
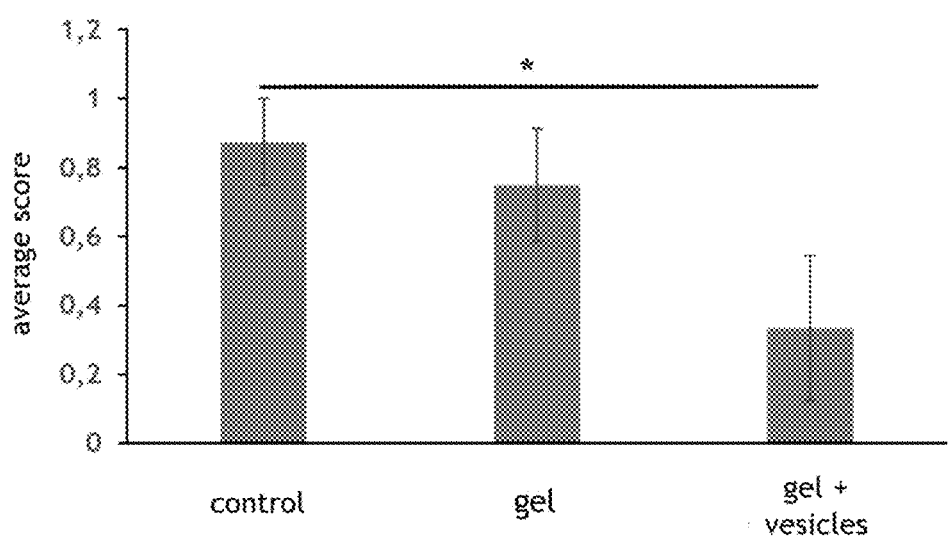
FIG. 25 illustrates the use of a composition of extracellular vesicles produced by the fluidic system as a pharmaceutical composition in a poloxamer gel for the treatment of fistula between the can and the caecum in rats.

FIG. 25 illustrates the use of a composition of extracellular vesicles EV produced by the fluidic system 1 as a pharmaceutical composition. A score is calculated from the observations presented in FIG. 24. A score equal to 1 is assigned when the opening of a fistula has feces and a score equal to zero is assigned when the opening of a fistula does not have feces. FIG. 25 illustrates the average score, for all caecostomies and for each of the conditions: control, "gel" and "gel+vesicles". The application of a gel comprising extracellular vesicles EV results in a reduction in the average productivity score of the fistulas compared to the groups of control and gel without vesicles and allows significantly reducing the presence of feces at the opening of the fistula in these conditions. Thus, the composition of extracellular vesicles EV produced by the fluidic system 1 can be used in the regenerative medicine.

Figure 26:
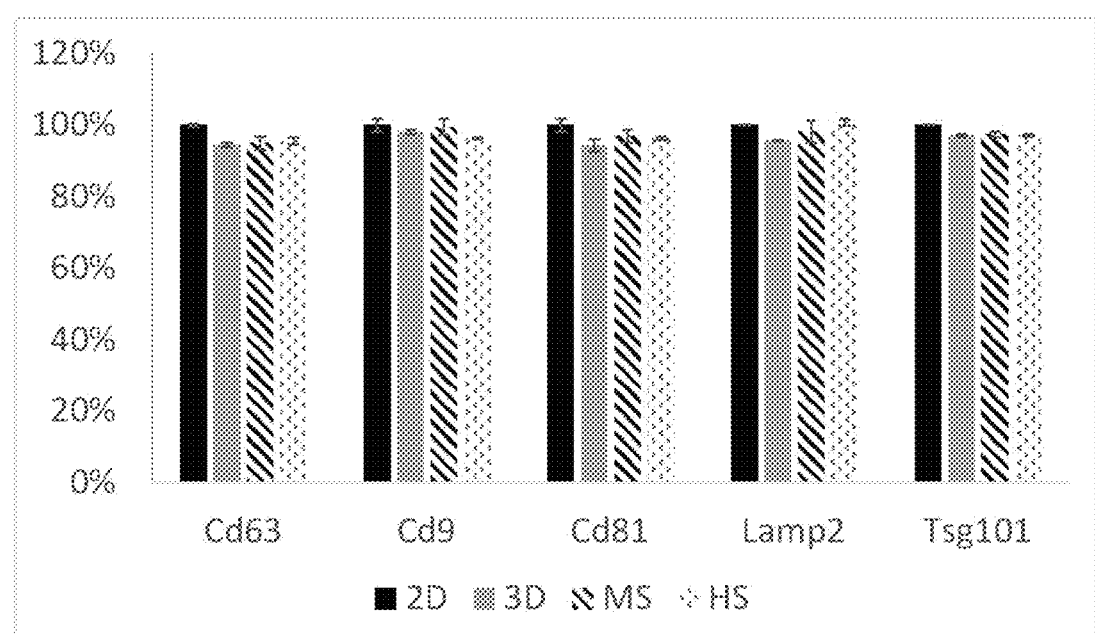
FIG. 26 illustrates the proteomic profile of extracellular vesicles produced by the method according to the invention compared to the profile of extracellular vesicles produced by the conventional production methods according to the prior art.

FIG. 26 illustrates the proteomic profile of extracellular vesicles produced by the method according to the invention compared to the extracellular vesicles produced by conventional production methods according to the prior art, more particularly the proteomic profile of markers conventionally used to characterise the extracellular vesicles.

The proteomic profile of the extracellular vesicles obtained by four different production methods were compared. A flask production method by serum deprivation for a duration of 72 hours (2D), a bioreactor production method by serum deprivation for a duration of 72 hours (3D), a medium speed bioreactor production method characterised by a Kolmogorov length equal to 50 µm for a duration of 4 hours (MS) and a high speed bioreactor production method characterised by a Kolmogorov length equal to 35 µm for a duration of 4 hours (HS).

The presence of biological markers conventionally used for characterising extracellular vesicles is thus observed. The presence and the amount of the common markers (CD63, CD9, CD81, lamp2 and TSG101) between the extracellular vesicles produced according to the method of the invention or the conventional production methods are similar.

In conclusion, the extracellular vesicles produced by the method according to the invention have a proteomic profile similar to the extracellular vesicles produced by the methods of the prior art. A proteomic profile characterised by the presence and the amount of markers conventionally used to characterise extracellular vesicles is understood as a similar proteomic profile.

The invention claimed is:

1. A method for ex vivo production of extracellular vesicles from producer cells, comprising:
   controlling an agitator causing a turbulent flow of a liquid medium in a container, the liquid medium being agitated for more than thirty minutes, the container comprising an output, the liquid medium comprising producer cells adhering on the surface of the microcarriers, the microcarriers being suspended in the liquid medium; and
   collecting the liquid medium comprising extracellular vesicles at the output of the container,
   wherein the agitator is controlled to cause the turbulent flow of the liquid medium to form vortices so that the turbulent flow has a Kolmogorov length of more than or equal to 33 µm and less than or equal to 75 µm, and
   wherein said turbulent flow method allows the production of the extracellular vesicles with a higher yield as compared to a serum starvation method for producing extracellular vesicles.

2. The method according to claim 1, wherein a separator depletes part of the liquid medium collected at the output of the container of extracellular vesicle, and wherein the part of the liquid medium is reintroduced into the container.

\* \* \* \* \*